(12) United States Patent
Larsen (10) Patent No.: US 10,184,103 B2
(45) Date of Patent: *Jan. 22, 2019

(54) U-SHAPE AND/OR NOZZLE U-LOOP FERMENTOR AND METHOD OF FERMENTATION

(75) Inventor: Ebbe Busch Larsen, Odense (DK)

(73) Assignee: UNIBO A/S (DK)

( * ) Notice: Subject to any disclaimer, the term of this patent is extended or adjusted under 35 U.S.C. 154(b) by 1090 days.

This patent is subject to a terminal disclaimer.

(21) Appl. No.: 13/139,501

(22) PCT Filed: Dec. 11, 2009

(86) PCT No.: PCT/DK2009/000250
§ 371 (c)(1),
(2), (4) Date: Jun. 21, 2011

(87) PCT Pub. No.: WO2010/069313
PCT Pub. Date: Jun. 24, 2010

(65) Prior Publication Data
US 2011/0244543 A1 Oct. 6, 2011

(30) Foreign Application Priority Data
Dec. 15, 2008 (DK) .................................. 2008 01780

(51) Int. Cl.
| C12M 1/00 | (2006.01) |
| C12M 1/34 | (2006.01) |
| B01J 19/00 | (2006.01) |
| B01J 19/18 | (2006.01) |

(52) U.S. Cl.
CPC ............ *C12M 41/40* (2013.01); *B01J 19/006* (2013.01); *B01J 19/1837* (2013.01); *C12M 29/18* (2013.01); *B01J 2219/00094* (2013.01)

(58) Field of Classification Search
CPC ...... C12M 29/18; C12M 41/40; B01J 19/006; B01J 19/1837; B01J 2219/00094
USPC .................................................. 435/41, 410
See application file for complete search history.

(56) References Cited

U.S. PATENT DOCUMENTS 6,492,135 B1 * 12/2002 Larsen .......................... 435/41
2004/0241790 A1 * 12/2004 Eriksen et al. ................. 435/41

FOREIGN PATENT DOCUMENTS

| EP | 0418187 A1 | 3/1991 |
| WO | WO00/70014 A1 | 11/2000 |
| WO | WO2003/016460 A1 | 2/2003 |
| WO | WO2004/026460 A1 | 4/2004 |

OTHER PUBLICATIONS

Sulzer, Static mixers, Accessed Sep. 28, 2018, Available online at: www.sulzer.com/en/ products/static-mixers.*
International Search Report for PCT/DK2009/00250, dated Sep. 16, 2010, 3 pages.

* cited by examiner

*Primary Examiner* — Jennifer M. H. Tichy
(74) *Attorney, Agent, or Firm* — Ware, Fressola, Maguire & Barber LLP (57) ABSTRACT

A fermenter and a method of fermentation in a U-shape and/or nozzle U-loop fermenter (100) comprising a U-part having an essentially vertical down-flow part (101), an essentially vertical up-flow part (102) and a substantially horizontal connecting part (103), which connects the lower ends of the down-flow part (101) and the up-flow part (102), a top part (104) which is provided above the U-part and has a diameter which is substantially larger than the diameter of the U-part, means for creating liquid circulation in U-part of the fermenter, and one or more gas injection points (110) for the introduction and dispersion of the gas(ses) into the fermentation liquid. The pressure may be controlled differently in certain zones of the fermenter by pressure controlling devices (105, 106, 108) e.g. by increasing the pressure in certain zones of the fermenter in relation to the pressure in the other zones of the fermenter, or decreasing the pressure in a zone of the fermenter in relation to the pressure in another zone of the fermenter in relation to the pressure in another zone of the fermenter.

13 Claims, 4 Drawing Sheets

U-SHAPE AND/OR NOZZLE U-LOOP FERMENTOR AND METHOD OF FERMENTATION

FIELD OF THE INVENTION

The present invention relates to a U-shape and/or U-loop fermenter and to a method of affecting a fermentation process.

More specifically, the invention relates to U-shape and/or nozzle U-loop fermenters and methods for the operation of the same, which are particularly appropriate for production processes with methanotrophic bacteria and similar processes, whereby one or more different gases and other nutrients are to be supplied to the fermentation liquid. The mass transport of gas from the gas phase and into the fermentation liquid is improved in order to obtain an optimally proceeding fermentation process with the highest possible yield of fermentation product in the shortest possible period of time.

Definitions

A fermenter or bioreactor is defined here as a vessel suitable for conducting fermentation or for employing biocatalysts.

A fermentation process is defined as the growth or maintenance of living biocatalysts under aerobic, anaerobic or partially aerobic conditions such that a desired product is produced, whether that product is the cells themselves or substances produced by the cells or converted by the cells.

Living biocatalysts encompass microbial cells, animal cells, insect cells, plant cells, viruses, phage, prions, amoebae, algae, fungi, bacterial, prokaryotic or eukaryotic cells.

Non living biocatalysts are dead cells or extracts from living or dead cells, e.g. enzymes.

BACKGROUND OF THE INVENTION

The use of biocatalysts such as microbial cells or enzymes to make products is well known and has been practised for centuries in what has become known as biotechnology processing. Typically in biotech processes microorganisms are cultivated in a tank (also called a fermentation tank, or simply a fermenter) into which the substrates necessary for the microorganisms to make the product are added.

Such cultivation processes typically occur in aqueous solutions (also called fermentation liquids, fermentation broths, or simply broths) containing a variety of substrates such as carbon sources as well as nitrogen sources, phosphates, sulphates plus a wide variety of other components depending on the microorganism used and the products to be made. In many cases the generic name fermentation is used for such processes which may be carried out in the presence or the absence of oxygen or air.

In many cultivations, the microorganisms used require oxygen, and this must be added. Oxygen is typically added as a gas by pumping compressed atmospheric air into the fermentation broth. Pure gaseous oxygen or oxygen enriched air may also be used as an oxygen source. Cultivations, in which oxygen is added, are called aerobic fermentations or aerobic cultivations. In some cases, other substrates used by the microorganisms are added as gases to the solution, and may for example be carbon sources such as methane. Waste products are also formed during fermentation. One waste product that is normally produced in the largest amount is carbon dioxide.

The addition of gaseous substrates such as oxygen or methane to fermentation liquid is problematic, since the microorganisms cannot use the gases directly. The gases must therefore be dissolved in the fermentation broth, after which they are taken up by the microorganisms and used as an energy source and/or for microbial growth. A generic problem in fermentation processes is therefore to solubilise enough of the gaseous nutrients in the broth to satisfy the demands of the microorganisms, particularly if the population or concentration of microorganisms is large (and the demand for gaseous substrates is high), or if the fermentation temperature is high, which tends to lower the solubility of the gaseous substrates in the fermentation broth.

The transfer rate of substances from the gas phase into the liquid phase can be improved if very small bubbles are used, or if a higher pressure (i.e. the pressure in the headspace of the fermenter is above atmospheric pressure) is used in the fermenter, or if the temperature of the broth is reduced. Since microorganisms are sensitive living cells, significant reduction of the temperature is not possible without affecting the growth rate of the microorganisms.

A large amount of energy is typically used in conventional fermentation tanks to ensure that sufficient amounts of the gaseous substrates are dissolved in the fermentation broth. Even so, many fermentation processes are limited by insufficient transfer of gases into the liquid phase.

Conventional fermenters are tall stirred tanks in which the mixing of gases with the fermentation liquid is effected by means of stirrer blades placed centrally in the fermenter. The stirrer blades generate turbulence in the liquid, which means that gas, usually injected at the bottom of the reactor, will be dissipated in the liquid in the form of small fine gas bubbles. The gaseous substrates are added at the bottom of the tank and must be pressurised to overcome the hydrostatic pressure in the tank into which they are pumped. This compression of gases requires significant amounts of energy.

This type of reactor provides a relatively homogenous mixing, i.e. that about the same concentrations of gases and substrates will be found whether measuring at the top or at the bottom of the reactor. But the vigorous mixing in order to create small gas bubbles and ensure optimal mixing in the tank also requires the use of excessive energy and further implies a significant heating of the fermentation liquid. The excessive use of energy renders this type of reactor uneconomical, especially for cheap products such as microbial cells, which are currently sold as animal food or fish food.

Other fermenter types have also been designed with the intention of reducing energy consumption for mixing but still ensuring sufficient mass transfer of gases to the liquid phase. These fermenters are often called air lift fermenters, jet loop fermenters or U-loop fermenters.

Different types of air lift reactors have been designed in order to avoid the mechanical stirring. The majority of these reactors are so-called loop reactors having two sections: an up-flow part and a down-flow part, which are interconnected at both ends. Gases are supplied as small bubbles at the bottom of the reactor in the up-flow part usually in a nozzle arrangement. The bubbles mix with the liquid, whereby the total density is reduced and the gas-liquid mixture ascends while being displaced by new liquid emerging from the down-flow part. The gas-liquid mixture moves up through the up-flow part of the reactor and releases gas bubbles at the top. Then, the liquid descends down through the down-flow part. In order to obtain a long residence time for the gas bubbles in the liquid. Airlift reactors are conventionally very tall slender reactors, and the gas must be supplied at a high pressure for overcoming the hydrostatic pressure at the bottom of the reactor. If the gas is air, this implies the use of compressors. Compression of air usually requires significant amounts of energy.

Airlift reactors have a relatively poor exploitation of the injected gas. Typically only 20-40% of the oxygen gas is utilized. It is often difficult to obtain a good and quick release of the gas bubbles from the fermentation liquid at the top of the reactor and separation of the gas phase thus produced (which may be rather foaming) from the liquid phase before the liquid flows into the down-flow part of the reactor. The gas phase, including significant amounts of waste gases from the fermentation, e.g. $CO_2$, is thus entrained in the broth, is then re-dispersed in the broth, which may lead to a reduced solubilisation of the substrate gases added to the fermenter.

The U-shape reactor has a simple design and is constructed with a view to provide non-compressed or nearly non-compressed substrate gas injection in combination with a long residence time for the gases and thus a high degree of exploitation of the injected gases. The top of the reactor is designed to achieve a good separation of gases and liquid.

In principle, the U-shape reactor is also a loop reactor. However, contrary to conventional loop reactors, the liquid circulation is effected by means of an in-line pump. The pump may be of the propeller pump type, wherein the propeller blades are designed for pumping a mixture of liquid and gas. Using pumps instead of injected compressed air or gases to create liquid circulation reduces the overall energy consumption during fermentation.

The substrate gases may be introduced at different locations in the U-shape loop. Typically they will be supplied at the upper end of the down-flow part of the loop. By introducing the substrate gases at the upper end of the down-flow part of the loop a nearly non-compressed injection is obtained, since the gases only have to overcome a hydrostatic pressure of some few meters. The gases may be introduced by means of gas dispensers providing for a distribution across the entire cross-section of the down-flow part of the loop. Fine dispersion of the gases in the liquid is effected by means of static mixing elements placed immediately downstream of the gas injectors (the mixing elements may be of e.g. Sulzer manufacture). The liquid flow in the down-flow part of the loop must be sufficiently high for carrying all the injected gas through the static mixers. In the static mixers, the gas phase is broken down into a large number of small gas bubbles, which are dispersed uniformly in the liquid. The bubbles are carried along with the liquid flow down through the down-flow part of the loop to its lower end and further on through a U-bend to the up-flow part of the loop. The gas bubbles may be re-dispersed (e.g. by means of a plurality of static mixing elements provided in both the down-flow and the up-flow part of the reactor) several times in the liquid.

The in-line pump is normally placed adjacent the U-bend, partly because it then assists in producing a re-dispersion of the gas in the liquid, and partly because it is practical to have it placed at the bottom of the fermenter.

The top of the fermenter is designed so that the up-flow part of the loop, via a bend, is passed horizontally and tangentially into the side of a widening of the upper end of the down-flow part of the loop. This particular construction feature assists in yielding a good separation of liquid and gas bubbles, as centrifugal forces act in the bend, and in the very widening of the upper end of the down-flow part of the loop a vigorous circulation of the liquid with corresponding accompanying centrifugal forces arises, which also brings about separation of liquid and gas bubbles. Thereby, one of the great problems associated with airlift reactors, viz. separation of the gas and liquid phases, is elegantly solved.

Furthermore, the U-shape reactor provides for a long contact time between the gas and liquid phases, as the injected gas is present both in the down-flow part and in the up-flow part of the loop. This means that an essentially higher utilization of the gas is obtained compared with conventional airlift reactors and stirred tanks.

Gas bubbles in liquids have a tendency to fuse together to larger bubbles (coalesce). This tendency contributes to making conventional airlift reactors ineffective inasmuch as the bubbles become larger and larger upward through the up-flow part, partly due to coalescence and partly due to a reduced hydrostatic pressure. In the U-shape reactor, this tendency in the up-flow part is counteracted by providing static mixers appropriately spaced apart at distances which depend on the medium applied. In the down-flow part, the increasing hydrostatic pressure counteracts the tendency to increased bubble sizes. To the extent that this effect cannot balance the coalescence of the gas bubbles, static gas mixers are provided for re-dispersion of the gases by static mixers.

The amount of gas, which may advantageously be dispersed in the liquid, depends on the hydrostatic pressure. In the case of tall reactors, it will therefore be advantageous to have several locations for the introduction of gases in the down-flow part. The only requirement with respect to the gas inlets is that at least one static mixing element is placed immediately after each inlet for dispersing the gas in the liquid.

Examples of airlift fermenters may be seen in EP 306466 A or U.S. Pat. No. 5,342,781 A.

Examples of U-loop fermenters of the above mentioned type are disclosed in EP 185407 A, EP 418187 A, EP 1183326 B and WO 03/016460 A1.

In EP 1183326 B and WO 03/16460 A1, which are considered to describe the closest prior art of the present invention, the fermentation process is controlled using sensors and analyzers in the fermenter delivering signals to data processing units, which then control the addition of gaseous substrates and other process parameters.

In WO 03/16460 A1 a substantial part of the U-loop in the reactor is horizontal in order to overcome problems a rising from an increasing hydrostatic pressure. This construction of the fermenter may result in gas pockets building up in the top of the horizontal part of the U-loop, and thus, reducing the liquid volume in the fermenter and reducing the overall productivity of the fermenter.

Nevertheless, the transfer of gases between the gas phase and the liquid phase in such fermenters is still too poor for producing inexpensive products in a fermentation process.

Gas mass transfer may be improved by increasing the pressure in the headspace (i.e. the space above the liquid surface in the fermenter) e.g. up to 1 bar or more above atmospheric pressure. This increase in pressure in headspace increases the pressure in the entire fermenter.

One problem with increasing the pressure in the fermenter is that the release of waste gases from the fermentation liquid is reduced when increasing the pressure. The energy employed for pressurising the headspace cannot be recovered. If the carbon source is supplied as a gas, e.g. methane, then explosive gas mixtures in the headspace may arise more easily when the pressure is increased.

One of the waste products produced in large amounts in fermentation processes is carbon dioxide ($CO_2$). All microbial cells produce carbon dioxide, which passes out of the cell and into the fermentation liquid. The carbon dioxide must then be transferred to the gas phase before it can be released from the fermenter. The solubility of the gases, including carbon dioxide, in the fermentation liquid is increased by increasing pressure. Thus, a higher pressure in the fermenter will reduce the release of carbon dioxide to the gas phase in the fermenter, resulting in a higher concentration of carbon dioxide in the fermentation broth. A high concentration of carbon dioxide in the fermentation liquid causes a reduced productivity of the cells in the fermenter and thereby a reduced overall productivity in the fermentation process.

Although the above-mentioned references also deal with optimisation of fermenters and methods of fermenting in which the gases supplied to the fermenter are more expensive gases, such as oxygen enriched air, pure oxygen and/or methane, there is still a need for further improvement of the overall productivity of the fermenters and the fermentation processes and especially further improvement of the utilisation of the substrate gases added to such fermentations.

No fermenter, fermenter or tank suitable for cultivation of living cells has previously been described that permits the pressure to be increased at will in certain parts of the fermenter, while the pressure is substantially equal to or even lower than atmospheric pressure in other parts of the reactor.

SUMMARY OF THE INVENTION

The object of the invention is to improve the mass transfer of the gaseous substrates into the liquid phase where they are available to the biocatalysts (e.g. the microorganisms) in an energy efficient manner.

It is also an object of the invention to improve the efficiency of the waste gas removal by improving waste gas transfer from the liquid phase into the gas phase for removal from the fermenter, even when the fermenter is operated under increased pressure.

These objects are achieved with the U-shape and/or nozzle U-loop fermenter according to the invention, which comprises a U-part having an essentially vertical down-flow part, an essentially vertical up-flow part and a U-bend having a substantially horizontal connecting part, which connects the lower ends of the down-flow part and the up-flow part, a top part which is provided above the U-part and connects the upper end of the down-flow part and the upper end of the up-flow part, the top part having a diameter which is substantially larger than the diameter of U-part, liquid circulation means in the U-part of the fermenter, an outlet, preferably placed in the top part or the horizontal connecting part of the U-part of the fermenter, for withdrawing fermentation liquid, and one or more gas injection points, which, according to wishes and demand, are placed in the down-flow part, the horizontal connecting part and/or the up-flow part, and having mixing members for dispersion of the gas(ses) introduced into the fermentation liquid, characterized in that a first pressure controlling device is inserted in the U-part of the fermenter for increasing the pressure in at least a first zone of the U-part in the fermenter in relation to the pressure in another zone, which includes the top part of the fermenter, the first pressure controlling device is preferably inserted in the top end of the down-flow part or in the connection part connecting the top part and the down-flow part, and a second pressure controlling device is inserted in the U-part of the fermenter and downstream of the first pressure controlling device when seen in the flow direction of the fermentation liquid.

The first pressure controlling device may be a valve (e.g. commercially available valve types), a pump, e.g. a propeller pump, a lobe pump, or a turbine pump, or the pressure may be increased by injection of pressurized air or another gas, e.g. an inert gas. The first pressure controlling device is preferably a propeller pump, which also creates liquid circulation in the fermenter.

The second and optionally a third pressure controlling device may be placed in the down-flow part, the up-flow part, or in the horizontal connecting part, but preferably the second pressure controlling device is in the upper half part of the up-flow part. The third optional pressure controlling device is preferably placed in the upper half part of the up-flow part and downstream to the second pressure controlling device when seen in the flow direction of the fermentation liquid. The second and/or third pressure controlling devices are chosen among a group of devices comprising a valve (e.g. commercially available valve types), a static mixer being constructed to optimize the pressure loss according to the pressure drop required in the fermenter, a hydrocyclone, a pump (e.g. a propeller pump, a lobe pump or a turbine pump), a pressure controlled valve, a plate with holes, nozzles or jets or a narrowing of the diameter or cross-section of the fermenter part in which it is placed.

Another object of the invention is to permit flushing of the headspace to improve waste gas removal and reduce the risk of explosive gas mixtures being formed in the headspace of the fermenter. This is achieved by placing gas flushing means in the top part, such as devices for adding and/or removing a gas in a headspace. The gas flushing means are preferably placed above the liquid surface for creating a gas flow of flushing gas co-currently, con-currently or cross-currently to the liquid flow in the top part of the fermenter. The gas adding means may also be placed below the liquid surface in the top part. Alternatively or additionally, waste gas removal may be increased by reducing the pressure in the headspace by applying suction or a vacuum, thus reducing the pressure in the headspace and/or by installing flow modifying means in the top part.

The invention also permits the energy applied to increase the pressure to be recovered for reuse. This is achieved by connecting the second, and optionally the third pressure controlling device to a brake or a generator for decreasing the pressure with the propeller pump. If a generator is connected to the second and/or third pressure controlling device, some of the energy applied to the system may be collected, thus reducing the overall energy consumption of the system.

Another object of the invention is to provide an improved method of fermentation in which the utilisation of added gaseous substances is improved.

Therefore, the invention also relates to a method of performing a fermentation process, in which at least one of the substrates is a gas, comprising adding fermenting microorganisms, necessary substrates, such as nutrient salts, pH adjusting components and water, and at least one gaseous substrate component into a U-shape and/or nozzle U-loop fermenter, and fermenting while the fermentation liquid is circulated in the fermenter by liquid circulating means, withdrawing a product stream from the fermenter and recycling recovered fermentation liquid (supernatant), if any, to the fermenter, characterized in comprising the steps of controlling the pressure differently in the circulating fermentation liquid in at least two different zones in the fermenter by increasing the pressure in at least a first zone of the U-part in the fermenter in relation to the pressure in another zone of the fermenter, thereby increasing the mass transfer of the at least one added gaseous substrate component from the gas phase into the liquid phase in that zone, followed by reducing the pressure in relation to the pressure in the first zone of the U-part, in the circulating fermentation liquid before it enters another zone, by means of at least a second pressure controlling device before the circulating fermentation liquid enters the top part of the reactor, which initiates liberation of gases from the liquid phase, and releasing gases trapped in the circulating fermentation liquid in the top part of the fermenter.

The productivity of the fermentation process is further optimised in that the circulating fermentation liquid experiences an alternating pressure during circulation in the fermenter and has an increased mass transfer and solubility of substrate gases into the liquid phase in the zone having an increased pressure. The productivity is also improved by release of gases, such as waste gases from the circulating fermentation liquid, which is increased in the zones where the pressure is reduced.

The method may be further improved by creating a third zone between the second pressure controlling device and a third pressure controlling device and controlling the pressure differently in the circulating fermentation liquid in each of the three different zones, e.g. by increasing the pressure in the first zone by the first pressure controlling device, and decreasing the pressure in the subsequent two zones in two steps by the second and third pressure controlling devices.

The object of the method according to the invention is also achieved by applying a pressure in the first zone preferably of 0.5-5 bar above atmospheric pressure and decreasing the pressure correspondingly in the following one or more zones.

Another object of the method according to the invention is to improve the gas separation of waste gases in the fermenter. This may be achieved by creating a gas flow of flushing gas for flushing the headspace co-currently, con-currently or cross-currently to the liquid flow in the top part. Gas separation may also be further improved by adding the flushing gas (e.g. air, $CO_2$ or an inert gas or mixtures thereof) in the top part below the liquid surface for increasing stripping of gases from the fermentation liquid in the top part and into the headspace. This may also be achieved by the fermentation liquid passing flow modifying means in the top part.

Another embodiment of the method according to the invention is an improved methanotrophic fermentation process in which at least one of the gases introduced into the fermentation liquid is methane or natural gas, and additionally at least one gas is introduced, which is either atmospheric air, pure oxygen or atmospheric air enriched with oxygen. The nitrogen source may be ammonia gas, which is introduced into the fermentation circulation loop.

Another embodiment of the method according to the invention is an improved methanotrophic fermentation process in which the methanotrophic bacteria used in the fermentation are *Methylococcus Capsulatus*. Optionally, one or more heterotrophic bacteria is added to the methanotrophic fermentation liquid. The preferred heterotrophic bacteria are chosen from *Alcaligenes acidovorans* (NCIMB 13287), *Aneurinibacillus danicus* (NCIMB 13288) and *Bacillus firmus* (NCIMB 13289) and combinations thereof.

Fermentation in the U-shape and/or nozzle-U-loop fermenter can be carried out in batch, batch fed or continuous mode. It is preferred to run the fermenter in a continuous mode after a start up phase. Continuous operation may be conducted as a chemostat, pH-stat, productstat or other continuous modes, as known by the skilled person, but preferably as a chemostat.

In a preferred embodiment, the fermenter is run in continuous operation mode, in which the productivity is optimised and the consumption of raw materials is minimised. Ideally, the fermenter may be run continuously for an extended period of time, e.g. many months without being shut down, but it is preferred to run the fermenter for a month before shutting down. During operation it should reach a steady state in which the majority of variables, including productivity, are essentially stable, i.e. varying less than 50% between three measurements, and preferably less than 10% between five measurements, taken half a residence time apart (where residence time is due to dilution rate).

The invention is considered to have special relevance for the production of so-called single cell protein (SCP) by continuous culture fermentation processes, e.g. by *Methylococcus capsulatus*, although the fermenter may be used for any fermentation process in which at least one substrate component is a gas, e.g. fermentation of other microorganisms, including genetically modified microorganisms or waste water treatment processes.

Biocatalysts

Suitable biocatalysts used in the process and the fermenter according to the invention may preferably be living cells, e.g. microorganisms of natural origin, i.e. wild types, specially selected mutated types or genetically modified types that may be used to produce single cell protein, enriched single cell protein, protein or peptide extracts, cell extracts, or preparations containing particular beneficial substances to be used for example for food or feed or to be delivered in order to improve or optimise the health, performance or well being of humans or animals, such as, but not limited to cloven hoofed animals (e.g. cattle, goats, sheep, pigs, etc.), poultry (e.g. fowls, chicken, ducks, goose/geese, turkey, etc.), fish (e.g. salmon, halibut, trout, cod, or other species bred in captivity) or shellfish (e.g. molluscs such as mussels, oysters or scallops).

The biocatalysts are preferably living microorganisms. Fermentation of the microorganisms may be carried out using pure cultures or using blends/a mixture of different microorganisms, e.g. for production of baker's yeast, single cell protein (SCP). The fermentation process may also result in biotransformations (i.e. microbial conversion of different chemicals to other useful chemicals), or production of intracellular or extracellular enzymes, proteins or hormones for use in different industries or in certain products, (e.g. pharmaceuticals, nutraceuticals or compounds for use as diagnostic or analytic agents).

The preferred bacteria for use in the invention are those capable of producing single cell protein, especially a culture comprising methanotrophic bacteria, which may optionally be combined with one or more species of other bacteria, e.g. heterotrophic bacteria.

Alternatively, the fermenter may be used for the fermentation of methylotrophic fungi or yeasts such as *Pichia stipitus* or *Pichia pastoris*. *P. stipidus* and *P. pastoris* are both capable of metabolising methanol and may be suitable for GMO-production.

The preferred methanotrophic bacteria are species of the *Methylococcus* family, especially *Methylococcus capsulatus*, which utilize methane or methanol as a carbon source and ammonia, nitrate or molecular nitrogen as a nitrogen source for protein synthesis.

*M. capsulatus* metabolises the methane in natural gas into biomass and carbon dioxide. *M. capsulatus* is also able to metabolise methanol instead of methane. Natural gas frequently contains 5-10% ethane and higher hydrocarbons, and *M. capsulatus* can only oxidize these hydrocarbons into the corresponding alcohols, aldehydes and carboxylic acids, but cannot oxidize these completely to carbon dioxide and water or utilize them for biomass production. Therefore, a pure culture of *M. capsulatus*, which is supplied with natural gas, will accumulate acetic acid and other carboxylic acids due to the content of higher hydrocarbons in the natural gas. Accumulated high concentrations of carboxylic acids inhibit the growth of *M. capsulatus*. Therefore, it may be useful to co-ferment one or more strains of heterotrophic bacteria with the methanotrophic bacteria for digesting higher hydrocarbons (alcohols, carboxylic acids, etc.) e.g. ethanol, acetate, citrate, etc. or degradation products of partially digested dead or decaying biomass.

Therefore, the fermentation liquid may be supplemented with one or more heterotrophic bacteria or yeasts (e.g. *Saccharomyces* and/or *Candida*). The co-fermentation is preferably carried out using three heterotrophic bacteria, which are selected for obtaining a fermentation ecosystem in which all product niches are occupied. Their main function is to exploit acetic acid and other carboxylic acids and degrade them to carbon dioxide, so that carboxylic acid accumulation is avoided.

The following heterotrophic bacteria are particularly useful to co-ferment with *M. capsulatus*: *Ralstonia, Bacillus brevis, Brevibacillus agri, Alcaligenes acidovorans, Aneurinibacillus danicus* and *Bacillus firmus*. Suitable yeasts may be selected from species of *Saccharomyces* and/or *Candida*.

The preferred combination of bacteria is a co-fermentation of *M. capsulatus* with *Alcaligenes acidovorans* (NCIMB 13287), *Aneurinibacillus danicus* (NCIMB 13288) and *Bacillus firmus* (NCIMB 13289).

The fermentation broth in the fermenter is preferably continuously provided with the required amounts of water and nutrient salts, such as ammonium/ammonia, magnesium, calcium, potassium, iron, copper, zinc, manganese, nickel, cobalt and molybdenum in the form of sulphates, chlorides or nitrates, phosphates and pH controlling components, i.e. acids and/or bases, as normally used by the skilled person, e.g. sulphuric acid ($H_2SO_4$), nitric acid ($HNO_3$), sodium hydroxide (NaOH), potassium nitrate ($KNO_3$). The latter is also a suitable nitrogen source for *M. capsulatus*.

DETAILED DESCRIPTION

The invention will now be described further with reference to the drawings in which.

The principles of a U-loop fermenter will now be explained with reference to FIG. 1, which shows a prior art U-shape fermenter as disclosed in EP 1183326 B, which belongs to the inventor of the present invention and is hereby incorporated by reference.

Figure 1:
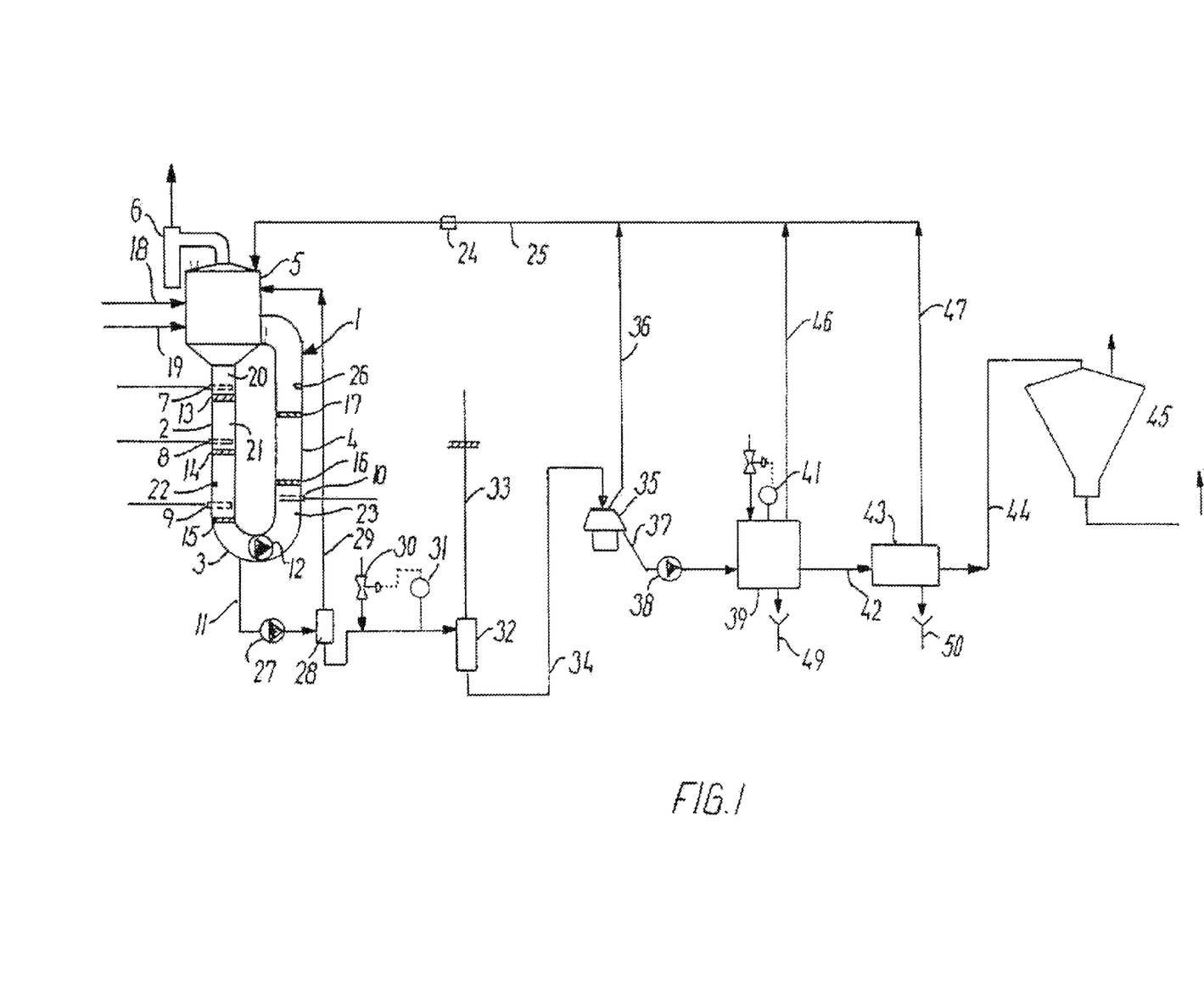
FIG. 1 is a schematic drawing of a cross-section of a prior art fermenter disclosed in EP 1183326 B.

In FIG. 1, 1 designates the U-shape and/or nozzle U-loop fermenter and 2 designates the down-flow part of the fermenter, 3 its U-bend part, and 4 its up-flow part. 5 designates the top part of the fermenter, while 6 designates a venting tube for exhausting the gas or gases separated in the headspace of the top part. 7, 8, 9, 10 indicate members for introducing a gas, e.g. natural gas or methane, ammonia, atmospheric air, pure oxygen or atmospheric air enriched with pure oxygen. 12 designates a pump installed in the U-bend of the fermenter for circulation of the broth in the fermenter. 13, 14, 15, 16 and 17, each indicates mixing members such as a static-mechanical mixing member for dispersion of the supplied gases into numerous small fine bubbles. 18 and 19 designates supply conduits for water and nutrient salts, such as phosphate, ammonium, magnesium, calcium, potassium, iron, copper, zinc, manganese, nickel, cobalt and molybdenum in the form of sulphates, chlorides or nitrates, phosphates and pH controlling components. 11 designates an outlet for draining off fermentation liquid with contents of produced biomass and/or other product substances for downstream processing. Sensors 20, 21, 22, 23, 24 are provided for sensing the concentrations of the gases and/or ions in question, e.g. $CH_4$ and $O_2$, and/or at least one of the ions phosphate, ammonium, nitrate and hydrogen ion (pH), and one or more thermo sensors 26 for sensing the temperature of the fermentation liquid in the fermenter loop. The sensors deliver signals to a data processing system (PC) (not shown), which controls the entire fermentation process, including downstream processing equipment.

The fermentation liquid withdrawn through the outlet 11 is pumped by a pump 27 to a gas separator 28, and the separated gases are returned to the fermenter through a conduit 29. $CO_2$ is released from the fermentation liquid in 32 after addition of acid 30, following which the fermentation liquid is passed to a down stream processing line comprising a first separator 35, such as a centrifuge, a sterilization unit 39 (e.g. UHT=Ultra High Temperature), a second separator 43, such as an ultrafiltration unit, and is finally passed to a drying unit 45, such as a spray drier. Liquid fractions, having a low content of biomass/product substances, from the first separator 35, the sterilization unit 39 and the second separator 43 are drained off through conduits 36, 46, 47, respectively, and are returned to the fermenter, e.g. after a short heat treatment, via the recirculation conduit 25.

Figures 2, 3:
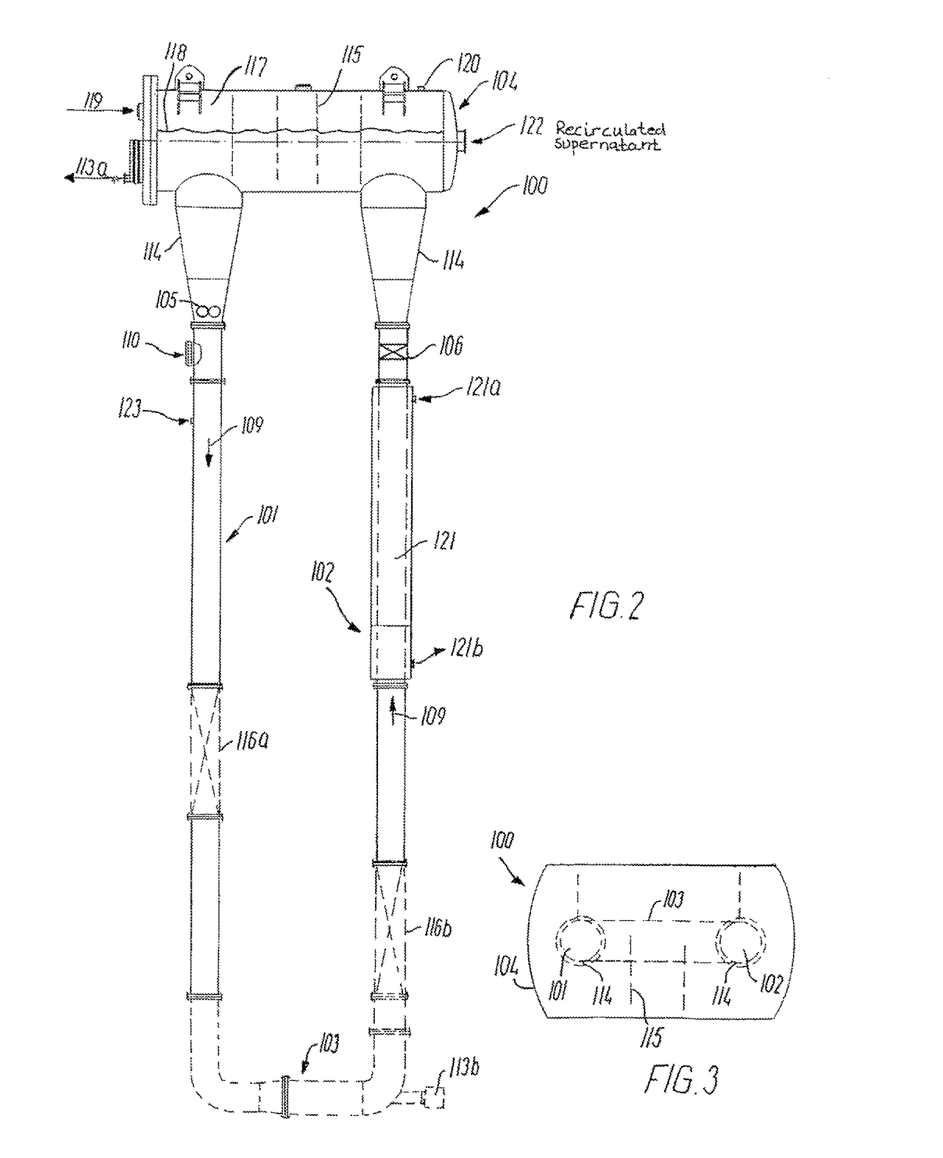
FIG. 2 is a schematic drawing of a first embodiment of a fermenter according to the invention.
FIG. 3 is a top view of the fermenter of FIG. 2.

FIG. 2 shows a novel fermenter according to the invention in which the pressure may be raised in certain zones of the fermenter while the pressure is substantially equal to atmospheric pressure, or optionally reduced below atmospheric pressure in other zones of the fermenter.

The fermenter is a U-shaped fermenter 100 having two legs, a down-flow leg 101 and an up-flow leg 102, which are being connected with a U-bend to establish a horizontal connecting section 103.

The cross-section of the legs and the connecting section is preferably substantially circular or oval, but the cross-section may also be polygonal, e.g. square, rectangular or hexagonal. The height of the legs in relation to the length of horizontal connecting section 103 (height legs:length lower connecting section) may be in the range between 100:1 to 1:100, preferably between 50:1 to 1:50 or 25:1 to 1:25, the most preferred ratio being 10:1. The overall volume of the fermenter may be in the range of 1 liter to 1000 m$^3$, preferably in the range of 0.2-500 m$^3$, optionally of 50-250 m$^3$. The diameter of the legs and the lower horizontal connecting section in relation to the height of the legs will depend on the overall volume of the fermenter needed, and may easily be calculated by any person skilled in the art.

The fermenter may contain one or more mixers 116a-116b e.g. static mixers or dynamic mixers necessary to modify mixing or modify the size of the gas bubbles in the fermentation liquid as necessary. The mixers 116a-116b may be placed in both legs of the fermenter, e.g. where gas is added and therefore mixing of gas and liquid is needed, or at places in the fermenter legs where gas redistribution is needed, e.g. due to increased coalescence of the gas bubbles or decreased hydrostatic pressure in the fermentation liquid. It is preferred to use static mixers, such as "Sulzer" type mixers. The number of mixers may be varied according to the needs for gas dispersion in the fermenter and is not limited to the number or places of the mixers 116a-116b shown in the figures. This is indicated in the figures where the gas mixers are drawn using broken lines. The need for gas dispersion in the fermenter depends on the microorganisms used and their concentration as well as the composition and/or physical properties (e.g. temperature, viscosity, etc.) of the broth.

The upper parts of the two legs 101,102 are connected by a top part 104 to close the fermenter. In a preferred embodiment, the fermenter is closed except for pipes and fittings (not shown) necessary to insert sensors or to add or remove substances to the fermenter. The top part 104 is preferably a container having a cylindrical or oval cross-section, and normally having a larger diameter than the legs of the fermenter. The cross-section of the top part 104 does not need to be cylindrical or oval, but may also be of polygonal shape, e.g. rectangular, square or hexagonal. The top part 104 is connected with straight or conical connection parts 114 for connecting the top part 104 to the legs 101,102 of the fermenter. The top part 104 of the fermenter is preferably designed to contain a substantial part of the fermentation liquid. The top part 104 may for example be designed to contain between 1% and 99% of the overall volume of the fermenter, but preferably between 10% and 60% of the overall fermenter volume. It is especially preferred that the volume of the top part is less than the volume of the U-part. When the fermenter is in operation, the top part 104 may be filled completely or partly with liquid. Preferably, the fermenter legs 101 and 102 and the connecting parts are flooded completely and the top part 104 is flooded partially with fermentation liquid, leaving a part of the volume, a headspace 117, in the top part 104 above the liquid surface 118 available for collection of gases. The size, i.e. both the diameter and the height of the fermenter may vary according to the needs of total fermenter volume. This is indicated in the drawings by the lowermost part of the U-part, i.e. the U-bend 103, drawn in broken lines.

The top part 104 may or may not contain liquid or gas flow modifying means 115 (shown in broken lines in FIG. 2 and FIG. 3) in order to assist mixing in the fermenter or to assist gas bubble release from the liquid. The gas or liquid flow modifying means 115 are such as, but not limited to baffles or static mixers, e.g. of the same type as in the fermenter legs.

One or more pressure controlling devices are placed in the fermenter to permit the pressure in the fermenter to be controlled, such that different zones of the fermenter experience a higher or lower pressure than other zones. It is preferred that one or more of the devices used to control the pressure are also used to circulate the liquid and/or the gas-liquid mixture in the fermenter.

In a preferred embodiment of the invention, a first pressure controlling device 105 is placed in the top of the first leg 101 (the down-flow leg) or in the connection parts 114, e.g. in the lower part thereof. The first pressure controlling device circulates the liquid in the fermenter, and at the same, time causes an increase in pressure when the liquid or the gas-liquid mixture passes through the first pressure controlling device. The first pressure controlling device 105 is preferably a pump, e.g. a propeller pump, a lobe pump or a turbine pump especially designed for circulating a gas-liquid mixture. Other suitable means for increasing the pressure and creating liquid circulation in the fermenter are e.g. addition of a pressurized gas, e.g. air or an inert gas in combination with a liquid circulating device, which may be a pump.

A second pressure controlling device 106 is placed in the fermenter 100, e.g. in one of the legs 101,102 or in the horizontal part of the U-bend 103, such that the pressure may be increased between the pressure controlling devices 105 and 106 when seen in the flow direction. When the pressure is increased in a zone in the fermenter, the solubility of the injected gases in the liquid phase is also increased. In a preferred embodiment, the second pressure controlling device 106 is placed in the middle to the top of the second leg 102. The pressure controlling devices 105,106 are preferably operated such that the pressure in the fermenter in the zone 105-103-106 is increased to a pressure above the pressure in the zone 106-104-105. However, if the entire fermenter is operated at a pressure above atmospheric pressure, the pressure controlling devices 105,106 may also be operated such that the pressure in the fermenter in the zone 106-104-105 is decreased to a pressure below the pressure in zone 105-103-106 e.g. by connecting a vacuum suction line (not shown) connected to the headspace (i.e. above the liquid surface 118) of the fermenter.

The pressure controlling device 106 may be chosen among a number of pressure controlling devices such as: a narrowing of the diameter/cross section of the leg 102 or of the connecting part 103, a plate with holes, jets or nozzles inserted in the leg 102 or the lower connecting part 103, a valve controlled by the pressure at one or more locations in the fermenter, a static mixer, a hydro cyclone or a pump, such as a propeller pump, a lobe pump or a turbine pump.

In one embodiment, the second pressure controlling device 106 is a static gas mixer. Static gas mixers are normally optimized for optimal mixing, and the pressure loss through the mixers are minimised. If a static mixer is used as a pressure controlling device, it should be constructed to optimize pressure loss according to the pressure drop required in the fermenter.

In an alternative embodiment, the second pressure controlling device 106 (see FIG. 5) may be a propeller pump. The propeller pump 106 may be driven by a motor 107 if it is to increase the pressure, e.g. due to pressure loss through the static mixers 116a, 116b. Alternatively, the propeller pump 106 is connected to a device 107 restricting the rotation and thereby decreasing the pressure. The device 107 which restricts rotation may be a brake, or, alternatively, it may be a generator which is capable of collecting some of the energy used to increase the pressure in the fermenter. The collected energy may be re-used at other locations of the system, thus reducing the overall energy consumption of the system.

In yet another embodiment of the invention, the pressure controlling device 106 is either a narrowing of the diameter/cross-section of the up-flow leg 102 or the horizontal part of the U-bend 103 or a plate with holes, jets or nozzles.

If necessary, a third pressure controlling device 108 (see FIG. 5) may be placed elsewhere in the fermenter, e.g. after the second pressure controlling device 106 in respect to the liquid flow direction 109 in the fermenter. The pressure may be decreased in the zone between the two pressure devices 106 and 108 in respect to the pressure in the first zone between the first pressure controlling device 105 and 106, i.e. the pressure is reduced in two steps before the broth enters the top part of the fermenter. The reduced pressure in the zone between the pressure controlling devices 106 and 108 may aid the coalescence of the gas bubbles and further assist in the release of waste gases, such as $CO_2$, from the fermentation liquid in the top part. The third pressure controlling device 108 may be of the same types as described for the second pressure controlling device 106, and is preferably also a narrowing of the diameter/cross-section of the leg 102 or the connecting part 103 or a plate with holes, jets or nozzles or a static gas mixer.

Figure 4:
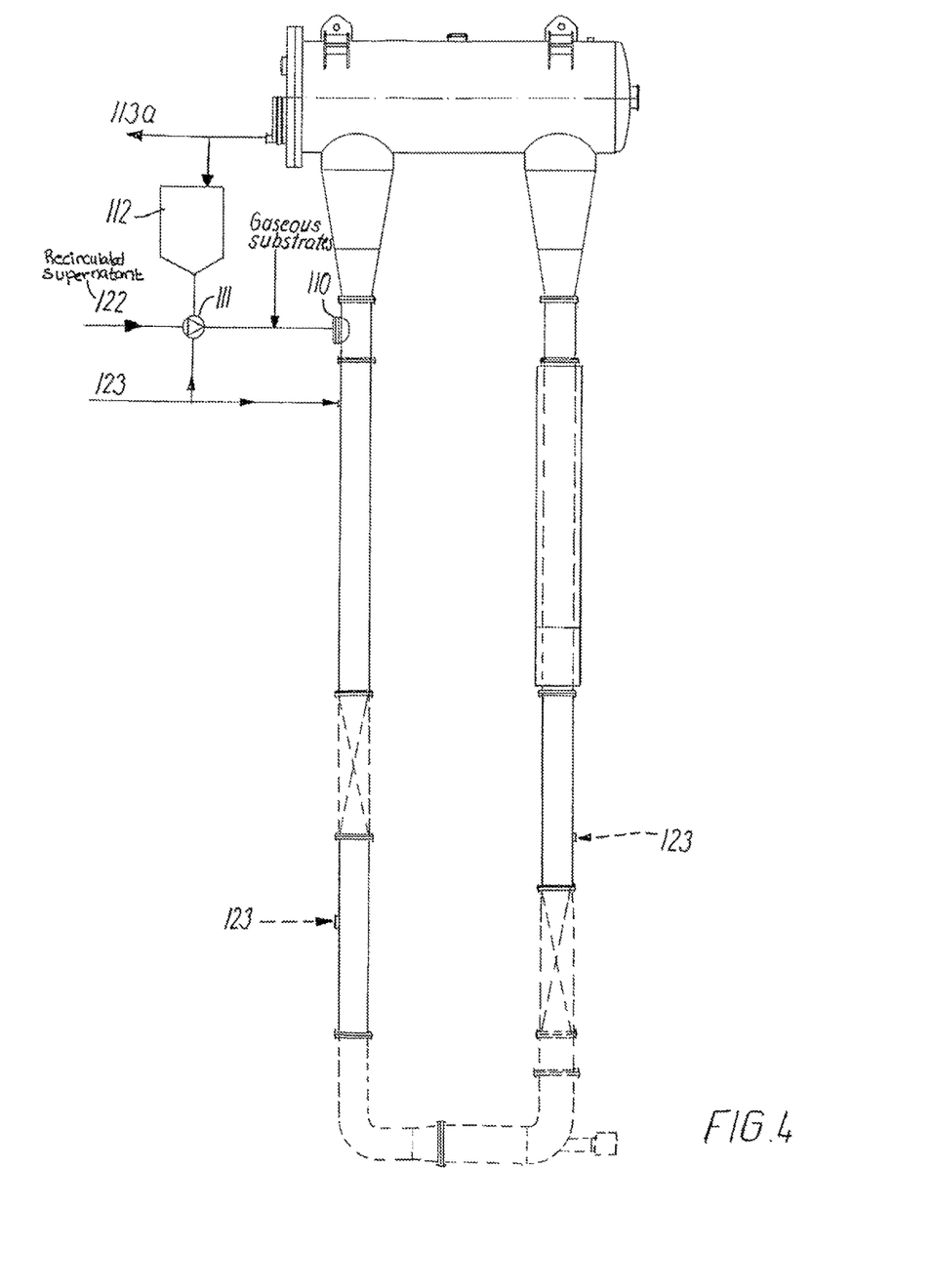
FIG. 4 is a schematic drawing of an embodiment of a fermenter according to the invention, showing an alternative layout of addition of gas and liquid to the fermenter.

The fermenter also contains one or more injection points 110 for adding gaseous substances directly to the broth in the fermenter. The gaseous substances may be added anywhere along the legs 101,102 or the lower connecting part 103 of the fermenter. In a preferred embodiment, the gas, e.g. pure oxygen, sterilised air or sterilised air enriched with oxygen is added through injection points 110 in the top of the first leg 101 of the fermenter. The injection points 110 are preferably placed closely after the flow/pressure increasing device 105 with respect to the liquid flow direction 109 in the fermenter. At this location in the fermenter, the hydrostatic pressure only contributes slightly to the total pressure in the liquid. Therefore, the need for compression of the gas, e.g. air or oxygen, is reduced to a minimum or even eliminated, which reduces the overall energy consumption of the system. Other gases, such as methane or ammonia may be added in the same way, e.g. in mixture with the air/oxygen through the injection points 110 or through other nozzles (not shown) placed in the down-flow leg, the up-flow leg or the U-bend of the fermenter. The injection points 110 for the addition of the gases may be single-flow nozzles and/or multi-flow nozzles. Single-flow nozzles add the gases directly to the broth, and multi-flow nozzles are e.g. jet nozzles driven by a pump 111 (see FIG. 4), which recirculates liquid taken from elsewhere in the fermenter, optionally via a holding tank 112, and mixes the liquid with the gases before or during injection into the fermenter. The liquid for use in multi-flow nozzles may e.g. be taken from the top part, a sub-flow of the broth withdrawn through an outlet (113a, 113b) from the fermenter and intended for downstream processing, liquid recirculated from downstream processing through a pipe 122 (see FIG. 4), or by pumping fresh liquid 123 (e.g. water and/or other liquid components of the broth) to nozzles at the injection points 110. Alternatively, the nozzle arrangement may comprise several nozzles of different construction, each being optimized for gas addition in different periods of the fermentation process. The nozzle arrangement for gas addition may e.g. comprise both single-flow and multi-flow nozzles, where the single flow nozzles are primarily used during start and initial fermentation, followed by the use of multi-flow nozzles during steady state fermentation. The nozzles for gas addition may optionally be arranged in a manifold-like construction. Additional gaseous substrate or other gaseous substances may be also be added at one or more other locations of the U-part of the fermenter. If the gases are added at one or more additional injection points, it is preferred to place extra static gas mixers in connection with the gas injection points.

Liquid substances, e.g. make-up water, aqueous solutions of substrate components, pH-regulating solutions may also be added at one or more locations 123 along the U-part of the fermenter, especially if one or more of the substrates act as a catabolic inhibitor to the microorganisms used.

The outlet 113a, 113b for transferring broth to downstream processing equipment may be placed in the top part 104 and/or in the U-bend 103. The outlet is preferably placed in the top part when the fermenter is run in continuous fermentation mode. Alternatively, or in addition to the first outlet 113a, a second outlet 113b may be placed in the U-bend, i.e. in the lowermost part of the reactor. The second outlet 113b may also be used when the fermenter is emptied entirely, e.g. for inspection or for sterilisation after a period of continuous fermentation. The second outlet 113b is also the primary outlet if the fermenter is run in batch mode or fed batch mode.

The pressure in the headspace 117 may be controlled by anyone skilled in the art, e.g. by releasing gas from headspace 117 through one or more valves (not shown) connected to an outlet 120.

The headspace 117 may also be flushed with a flushing or stripping gas to assist in the removal of $CO_2$ and other waste gases produced during fermentation or other gases present in the headspace 117. It is also possible to flush the headspace if methane is present in critical amounts in order to reduce or eliminate any risk of explosion. The flushing gas may be air, nitrogen, carbon dioxide itself or any combination of known gases suitable as a flushing gas. The flushing gas is added to the headspace through a device 119, such as a pipe and/or one or more nozzles in such a way that it flushes the liquid surface 118 and/or the headspace 117 and leaves the top part through an outlet 120. The flow of the flushing gas may flush the liquid surface and or headspace co-currently, con-currently or cross-currently in respect to the direction of the liquid flow in the top part. Preferably, a counter-current flow of flushing gas is used. The position of the inlet 119 and the outlet 120 for flushing gases is adjusted according to the flow direction of the flushing gases.

Alternatively, or in addition to flushing of the headspace, one or more of the gaseous substances may also be added below the liquid surface in the top part 104 of the fermenter. If the flushing gas, such as air or an inert gas, is added at the bottom of or at the inlet to the top part 104, it may assist in stripping off any rest of solubilised waste gases, especially $CO_2$, from the fermentation liquid and into the headspace 117.

The U-part of the fermenter may also be equipped with a temperature regulating device 121 for heating or cooling the circulating fermentation broth. The temperature regulating device 121 is preferably a cooling and/or heating jacket mounted on the up-flow leg 102 as shown on FIG. 2, having fittings 121a, 121b for circulating heating or cooling media through the jacket. Alternatively, the heating/cooling jacket may be mounted on the down-flow leg 101. If needed, the fermenter may be equipped with more than one temperature adjusting device or heating/cooling jacket, e.g. both on the down-flow leg 101 and the up-flow leg 102.

One or more pressure sensing devices (not shown) are placed in the fermenter. Preferably, at least one pressure sensor is placed in each of the zones of the fermenter operated under different pressures. The pressure sensing devices are connected to a process control system, e.g. a computer, which may control the pressure controlling devices 105, 106, 108 in order to maintain an optimal pressure in each of the zones in the fermenter. One or more sensors (not shown) for determining dissolved oxygen (DO) may also be placed in the fermenter in order to detect if the oxygen level in the fermenter is kept within a predefined range, which depends on the microorganism or microorganisms used in the fermentation.

Additional sensors, e.g. for measuring temperature, pH, conductivity measurements, oxidation reduction potential and different ions present in the broth, e.g. ammonia, nitrite, nitrate, phosphates, etc., are performed on the circulating broth and/or the recirculated supernatant from down stream processing using commercially available sensors. The sensors include biosensors, electrochemical sensors, e.g. ion sensitive electrodes or sensors based on FIA (flow injection analysis) and optical measurements, e.g. spectrophotometric devices. A Near Infrared (NIR) probe may also be used for measuring several different components in the broth or in the cells in the fermenter, e.g. concentration of cells, amino acids, methanol, ethanol and/or different ions. The fermenter may also be equipped with a mass spectrometric (MS) sensor or an electronic nose for determining the concentration of gaseous and volatile components (e.g. $CO_2$ and/or $CH_4$) in the headspace 117. The MS sensor or the electronic nose may control the pressure applied in the fermenter and/or the addition of gaseous components, e.g. methane and/or air/oxygen and/or the addition of gaseous ammonia or the ammonia/ammonium in solution. A high speed camera may be installed in the U-part of the fermenter, preferably in connection with gas injection, for determining the bubble size of the gases in the broth. The bubble size may be determined by image processing of the data from the high speed camera.

The recirculated supernatant 122 may also be added to the top part of the fermenter as in FIG. 2, or it may be added at one or more positions in the U-part of the fermenter. Return of supernatant from downstream processing reduces the overall consumption of substrates, carbon and minerals, thus reducing the costs of the fermentation process.

The connection parts 114 may or may not contain vortex hindering means (not shown), e.g. baffles or the like according to needs.

The fermenter is normally run in continuous operation mode, after cleaning and a sterilisation procedure, followed by a start period in which water, necessary nutrient salts and the microorganisms are added to the fermenter. The fermentation broth is circulated in the fermenter, mainly by the first pressure controlling device 105. Then addition of gaseous substrates is initiated, and fermentation is started. Fermentation broth is continuously withdrawn from the fermenter for downstream processing when the microorganisms have reached a concentration of approximately 0.5-10%, and preferably 1-5% (by dry weight). Then withdrawing of fermentation liquid through the outlet 113a is initiated simultaneously with the addition of make-up water, aqueous substrate 123 and/or recirculation of supernatant 122 at a dilution rate depending on the microorganisms used in the fermentation. If M. Capsulatus is used, the dilution rate is e.g. 0.01-1.5 $h^{-1}$ and preferably between 0.2-0.8 $h^{-1}$. Addition of substrate components in liquid solution, additional water, recirculation of supernatant as make-up for the withdrawn broth and substrate gases are controlled by a computer receiving data from the gas sensors in the headspace, ion sensors or analyzers, thermo sensors, pressure sensors, etc. and calculating the necessary amounts of each component for obtaining optimized growth of the microorganisms. The hydraulic circulation time in the fermenter is normally around 10-15 seconds depending on the size of the fermenter and the effect of the first pressure controlling device.

In one embodiment of the method, the fermenter is divided into two zones by at least two pressure controlling devices 105,106 and the two zones are maintained at different pressures. The first fermenter zone normally comprises the part of the U-part between the first 105 and the second 106 pressure controlling device and the second zone preferably comprises the top part 104 and optionally the upper part of the up-flow leg. The second pressure controlling device 106 aids in maintaining the applied pressure in the first zone and reduces the pressure in the circulating broth before it enters second zone. The increased pressure in the first zone in the fermenter raises the mass transfer from the gas phase and into the liquid phase and hereby increases the concentration/amount of the gaseous substrate(s) available to the microorganisms. When the second pressure device 106 reduces the pressure in the second zone, the solubility of the gases in the fermentation broth is reduced. This increases the mass transfer of solubilised gaseous components from the broth and into the gas phase and improves the coalescence of gas bubbles. As a result, the separation of waste gases in the top part is improved significantly in the method of the invention compared to prior art U-shaped or nozzle U-loop fermenters and methods.

Figure 5:
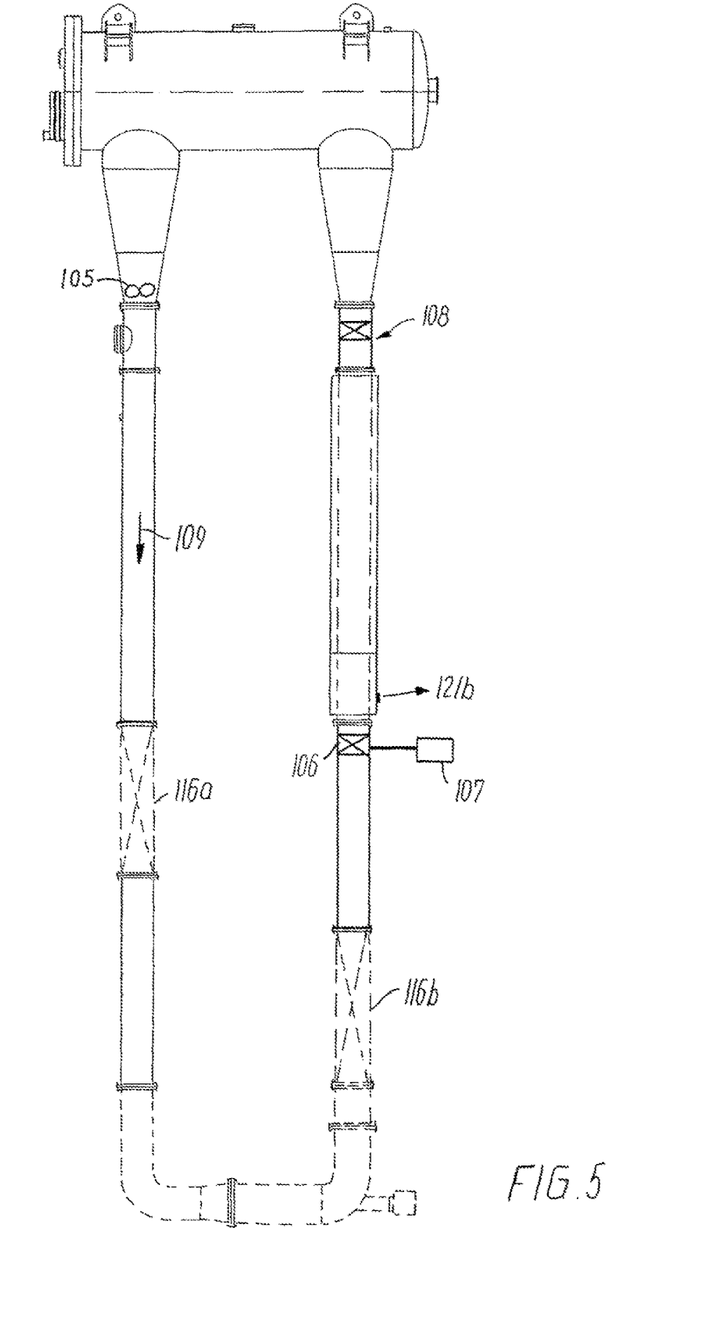
FIG. 5 is a schematic drawing of an embodiment of a fermenter according to the invention having three pressure controlling devices.

In an alternative embodiment of the method, the fermenter may be equipped with three or more pressure controlling devices. The second pressure controlling device 106 re-establishes pressure losses occurring through the fermenter, e.g. in the mixers, followed by a third pressure controlling device 108 which reduces the pressure in the following zone comprising the top part 104 of the fermenter. The second pressure controlling device 106 may also decrease the pressure slightly in the fermenter, which is then further decreased by the third pressure controlling device 108 before the fermentation broth enters the top part 104. In the latter embodiment, the fermenter is divided into three zones in which the pressure is reduced in two steps before the broth enters the top part 104. This two-step reduction of the pressure further improves the mass transfer of gases from the broth and coalescence of gas bubbles and hereby increases separation of waste gases in the top part 104.

The pressure is mainly controlled in the different zones by the computer using input from the pressure sensors in the fermenter. The first pressure controlling device 105 applies a pressure to the broth, which is up to 8 bars or more and preferably 0.5-5 bars. The hydrostatic pressure increases the pressure even further through the down-flow leg and decreases the pressure correspondingly during passage through the up-flow leg of the fermenter. The contribution of the hydrostatic pressure depends on the height of fermenter. If the pressure is reduced by applying a suction or vacuum in the top part 104 during fermentation, e.g. for assisting removal of waste gases, the absolute pressure applied in the first zone is reduced correspondingly. The pressure difference between the pressure applied by the first pressure controlling device 105 in the first zone (i.e. the U-part) and the pressure in the top part 104 should preferably be 0.5-5 bars.

Gas separation in the top part may improved by flushing the headspace above the liquid surface in the top part using a flushing or stripping gas. The flushing gas is introduced co-currently, con-currently or cross-currently to the liquid flow in the top part. Alternatively, the flushing gas may be introduced into the top part below the liquid surface. The flushing/stripping gas then bubbles through the fermentation liquid and strips of gases entrained in the liquid.

The temperature may be regulated during start and fermentation by adding a heating or cooling medium to the heating/cooling jacket 121.

The pressure and other variables are normally controlled in relation to setpoints or intervals in process control systems normally provided by the skilled person. The data from other sensors in the fermenter, and optionally in the recirculation supernatant line, are included in the control of parameters, e.g. pressure, temperature, substrate gas addition, pH adjustment, addition of make-up water, aqueous substrate media and/or recirculation of supernatant, in the system using e.g. Process Analytical Technology (PAT) and/or multivariate data analysis combined with multivariate process control.

During operation, the fermentation process should reach a steady state in which the majority of variables, including productivity, is essentially stable (i.e. varying less than 50% between three measurements, and preferably less than 10% between five measurements, taken half a residence time apart (where residence time is due to dilution rate).

Ideally, the fermenter may be run continuously for an extended period of time, e.g. many months without being shut down, but it is preferred to run the fermenter for a month before shutting down.

Downstream processing of the fermentation liquid extracted from the fermenter is essentially similar to the process described in EP 1183326 B and as shown in FIG. 1. Liquid fractions (supernatant), having a low content of biomass/product substances, from the first separator 35, the sterilization unit 39 and the second separator 43 are drained off through conduits 36,46,47, respectively, and are returned at 122 to the fermenter, e.g. after a short heat treatment, via the recirculation conduit 25. One or more of the fermenters according to the invention may be connected to a common downstream processing system.

The spray drying unit 45 may be omitted in downstream processing, if the product is to be used as a liquid concentrate. Optionally, the sterilising unit 39 may also be omitted on a part of or on the entire product stream.

In a preferred embodiment of the invention, the method is used for fermenting methanotrophic bacteria and especially for the production of SCP by *Methylococcus capsulatus*. *M. Capsulatus* is aerobic, i.e. requires addition of oxygen as pure gas or air, and uses methane or methanol as a carbon and energy source which is added as a gas (methane or natural gas) or as a liquid, e.g. in an aqueous solution (methanol). If natural gas is used as a source for methane for *M. capsulatus*, then the fermentation liquid is supplemented with one or more, e.g. up to three heterotrophic bacteria, which are selected so that their main function is to exploit acetic acid and other carboxylic acids and degrade them to carbon dioxide so that carboxylic acid accumulation is avoided. The preferred combination of bacteria is a co-fermentation of *M. capsulatus* with *Alcaligenes acidovorans* (NCIMB 13287), *Aneurinibacillus danicus* (NCIMB 13288) and *Bacillus firmus* (NCIMB 13289).

The fermenter may also be suitable for continuous fermentation for production of primary and secondary metabolites as well s chemicals which are not native to the host via genetically modifying the organism, (so called GMO) production of vanillin. Vanillin is toxic to the host organism and may inhibit growth or kill the host organism, if the concentration in the broth becomes high. If the fermenter is equipped with a vacuum or suction line in the headspace, then vanillin may evaporate in the headspace and hereby reduce the concentration of toxic vanillin in the broth. The vanillin may subsequently be extracted from the gas phase which is drawn from the head space of the fermenter.

EXAMPLE

Single cell protein is produced by a co-fermentation of *M. capsulatus* with *Alcaligenes acidovorans* (NCIMB 13287), *Aneurinibacillus danicus* (NCIMB 13288) and *Bacillus firmus* (NCIMB 13289) using natural gas as carbon and energy sources and atmospheric air enriched with pure oxygen as an oxygenation source. Ammonia is used as nitrogen source. In addition to theses gaseous substrates, the cultivation of *M. capsulatus* requires water, phosphate, and several minerals such as magnesium, calcium, potassium, iron, copper, zinc, manganese, nickel, cobalt and molybdenum (added as sulphates, nitrates or chlorides in a mineral mixture). Sodium hydroxide and sulphuric acid are used for pH adjustments. All chemicals are food grade. Phosphate is supplied in the form of phosphoric acid, minerals as sulphates, chlorides or nitrates.

After cleaning and sterilization, the U-shape fermenter, having a fermentation volume of 10 $m^3$, is filled with water, and the necessary nutrient salts and an inoculation culture of the co-fermenting microorganisms are added. A pressure of approximately 5 bars is applied to the top of the down-flow leg in the U-part of the fermenter, and liquid circulation is started by the first pressure controlling device (an in-line propeller pump). The pressure is reduced to atmospheric pressure by the second pressure controlling device (a pressure controlled valve) before the circulating broth enters the top part. Then the feed gases (natural gas, ammonia and oxygen as atmospheric air) are introduced just below the propeller pump into the fermentation liquid, until a steady state with a biomass content of 2-3% (w/w) solids is obtained. Then withdrawing of fermentation liquid through the outlet 113a is initiated simultaneously with supplying water and the mineral solution at a dilution rate of approximately 0.2 $h^{-1}$. Then, the supply of gases, nutrient salts and pH adjustment means is performed on the basis of in-line measurements of ammonium, phosphate and nitrate, oxygen, methane etc. by the sensors in the system.

During steady state fermentation the oxygen concentration is kept at a level below 10-25 ppm, the pH value is controlled to 6.5±0.3, and the temperature is maintained at 45° C.±2° C. If any significant or dangerous amount of methane is detected in the headspace (methane is detected by MS), the pressure and/or the addition of natural gas is reduced slightly. The average amounts of added and removed substances are shown in table 1.

TABLE 1

| Substances: | Amount per hour |
|---|---|
| Natural gas (calculated as Methane) added | 60 kg |
| Oxygen gas added | 200 kg |
| Air added | 600 kg |
| Water added | 2000 kg |
| Ammonia added | 10 kg |
| NaOH (1.5% w/w) added | 15 kg |
| Mineral mixture added | 20 kg |
| Broth withdrawn from fermenter | 2000 kg |
| Headspace flushing gas (air) added/removed | 10 $Nm^3$ |

The fermentation broth withdrawn from the fermenter is processed using downstream processing equipment described earlier and as shown in FIG. 1. A non-dusty agglomerate having a content of solids (TS) of approximately 94% by weight is obtained.

The average composition values of the SCP protein product are shown in table 2:

TABLE 2

| Composition | Weight % |
|---|---|
| Crude protein | 70.6 |
| Crude fat | 9.8 |
| Ash | 7.1 |
| Crude fibre | 0.7 |
| N-free extract | 11.8 |
| Total | 100.0 |

The invention claimed is:

1. A method of performing a fermentation process, in which at least one substrate is a gas, the method comprising:
adding fermenting microorganisms, substrates including nutrient salts, pH adjusting components and water, forming a fermentation liquid, and the at least one gaseous substrate into a U-shape and/or nozzle U-loop fermentor comprising a U-part having a down-flow part, an up-flow part and a connecting part that connects a lower end of the down-flow part and a lower end of the up-flow part, and a top part that is provided above the U-part that connects an upper end of the up-flow part and an upper end of the down-flow part,
fermenting while circulating the fermentation liquid in the fermentor using a liquid circulator,
withdrawing a product stream from the fermentor and recycling a recovered fermentation liquid or supernatant, if any, to the fermentor,
subjecting the circulating fermentation liquid to at least two different controlled pressures, including a high pressure, which is a pressure level above atmospheric pressure, and a relatively lower pressure by:
defining at least two controlled pressure zones in the U-part of the fermentor, a first controlled pressure zone located in the U-part between a first pressure controlling device and a second pressure controlling device located downstream thereof and including the connecting part, and at least one other controlled pressure zone located downstream of the second pressure controlling device and between the second pressure controlling device and the first pressure controlling device and including the top part therein,
controllably maintaining an increased pressure in the first controlled pressure zone in relation to a pressure controllably maintained in the second controlled pressure zone of the fermentor, thereby increasing the mass transfer of the at least one added gaseous substrate from the gas phase into the liquid phase in the first controlled pressure zone maintained at the increased pressure, followed by
controllably reducing a pressure of the circulating fermentation liquid, in relation to the increased pressure in the first controlled pressure zone, by passing the circulating fermentation liquid into the second controlled pressure zone located in the U-part before the circulating fermentation liquid enters the top part of the fermentor, controllably maintaining a reduced pressure in the second controlled pressure zone of the fermentor for liberating gases from the liquid phase in the second controlled pressure zone, and
releasing the liberated gases trapped in the circulating fermentation liquid in the top part of the fermentor,
wherein the first pressure controlling device is placed in the upper end of the down-flow part,
wherein the first pressure controlling device is selected from the group consisting of a valve; a pump; a propeller pump; a lobe pump and a turbine pump, and
wherein the second pressure controlling device is chosen among a group of devices comprising a valve; a hydrocyclone; a pump chosen from a group of devices comprising a propeller pump, a lobe pump, and a turbine pump; nozzles or jets or a narrowing of diameter.

2. The method according to claim 1, wherein the second pressure controlling device, is inserted in the U-part of the fermentor.

3. The method according to claim 1, further comprising defining a third controlled pressure zone between the second pressure controlling device and a third pressure controlling device, by positioning the third pressure controlling device below the top part downstream of the second pressure controlling device, and, subjecting the circulating fermentation liquid to a third controlled pressure, different from the increased pressure in the first controlled pressure zone and from the relatively lower pressure in the second controlled pressure zone, controllably maintaining the third pressure within the third pressure control zone as the circulating fermentation liquid passes through the third controlled pressure zone, such that the circulating fermentation liquid is maintained at three distinct pressures within each of the three controlled pressure zones.

4. The method according to claim 1, wherein the circulating fermentation liquid is subjected to an increased pressure in the first controlled pressure zone of 0.5-5 bars above atmospheric pressure.

5. The method according to claim 1, wherein the fermentation process is a methanotrophic fermentation process.

6. The method according to claim 5, wherein at least one of the gases introduced into the fermentation liquid is methane or natural gas and further comprising additionally introducing at least one gas, which is either atmospheric air, pure oxygen or atmospheric air enriched with oxygen.

7. The method according to claim 6, further comprising additionally introducing ammonia gas into the fermentation circulation liquid as a nitrogen source for the fermentation process.

8. The method according to claim 5, further comprising using methanotrophic bacteria in the fermentation process, the bacteria being *M. Capsulatus*.

9. The method according to claim 8, further comprising adding one or more heterotrophic bacteria to the fermentation liquid, the heterotrophic bacteria being selected from the group consisting of *Alcaligenes acidovorans, Aneurinibacillus danicus, Bacillus firmus*, or combinations thereof.

10. The method according to claim 8, further comprising adding one or more heterotrophic bacteria to the fermentation liquid, the heterotrophic bacteria being selected from the group consisting of *Alcaligenes acidovorans* as deposited under NCIMB 13287, *Aneurinibacillus danicus* as deposited under NCIMB 13288, *Bacillus firmus* as deposited under NCIMB 13289, or combinations thereof.

11. A method of performing a fermentation process, in which at least one of the substrates is a gas, the method comprising:
adding fermenting microorganisms, substrates including nutrient salts, pH adjusting components and water, forming a fermentation liquid, and at least one gaseous substrate component into a U-shape and/or nozzle U-loop fermenter having a down flow part, an up flow part and a top part, fermenting while circulating the fermentation liquid in the fermenter using a liquid circulator,
withdrawing a product stream from the fermenter and recycling a recovered fermentation liquid or supernatant, if any, to the fermenter,
controlling a pressure differently in the circulating fermentation liquid in at least two different zones in the fermenter by
increasing a pressure in at least a first zone of the U-part in the fermenter in relation to a pressure in another zone of the fermenter, by locating a first pressure increasing device in an upper end of the down flow part, thereby increasing the mass transfer of the at least one added gaseous substrate component from the gas phase into the liquid phase in the first zone, followed by
reducing a pressure on a second zone, in relation to the pressure in the first zone of the U-part, in the circulating fermentation liquid, by positioning at least one second pressure controlling device in a portion of the U-part downstream of the first pressure controlling device, the second zone provided before the circulating fermentation liquid enters the top part of the fermenter, which initiates liberation of gases from the liquid phase, and
releasing gases trapped in the circulating fermentation liquid in the top part of the fermenter,
wherein the first pressure controlling device is selected from the group consisting of a valve; a pump; a propeller pump; a lobe pump and a turbine pump, and
wherein the second pressure controlling device is chosen among a group of devices comprising a valve; a hydrocyclone; a pump chosen from a group of devices comprising a propeller pump, a lobe pump, and a turbine pump; a plate with holes, nozzles or jets.

12. The method according to claim 11, further comprising creating an intermediate zone between the second pressure controlling device and a third pressure controlling device positioned within the U-part of the fermentor, controlling the pressure within the intermediate zone by using the second and third pressure controlling devices, the intermediate zone located between the first zone and the second zone, which is displaced downstream of the third pressure controlling device and before the circulating fermentation liquid enters the top part of the fermentor, such that the method comprises subjecting the circulating fermentation liquid to three different pressures within the three different zones.

13. The method according to claim 11, wherein the step of increasing the pressure in the first zone comprises applying a pressure in the first zone of 0.5-5 bars.

* * * * *

UNITED STATES PATENT AND TRADEMARK OFFICE
CERTIFICATE OF CORRECTION

PATENT NO. : 10,184,103 B2
APPLICATION NO. : 13/139501
DATED : January 22, 2019
INVENTOR(S) : Ebbe Busch Larsen It is certified that error appears in the above-identified patent and that said Letters Patent is hereby corrected as shown below:

On the Title Page

Column 1, item (73) Assignee: "Unibo A/S" should be --Unibio A/S--.

Signed and Sealed this
Twenty-sixth Day of April, 2022

Katherine Kelly Vidal
*Director of the United States Patent and Trademark Office*